United States Patent
Ostermann et al.

(10) Patent No.: US 11,029,299 B2
(45) Date of Patent: Jun. 8, 2021

(54) CONTROL UNIT AND METHOD FOR CONTROLLING A GAS MEASURING DEVICE

(71) Applicant: Dräger Safety AG & Co. KGaA, Lübeck (DE)

(72) Inventors: Ulf Ostermann, Rümpel (DE); Christof Rodehorst, Lübeck (DE); Celina Fiedler, Hamburg (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days.

(21) Appl. No.: 16/754,446

(22) PCT Filed: Oct. 8, 2018

(86) PCT No.: PCT/EP2018/077322
§ 371 (c)(1),
(2) Date: Apr. 8, 2020

(87) PCT Pub. No.: WO2019/072763
PCT Pub. Date: Apr. 8, 2019

(65) Prior Publication Data
US 2020/0348279 A1    Nov. 5, 2020

(30) Foreign Application Priority Data
Oct. 12, 2017   (DE) .................. 10 2017 009 525.6

(51) Int. Cl.
*H04L 29/02* (2006.01)
*G01N 33/00* (2006.01)
*G08C 19/00* (2006.01)

(52) U.S. Cl.
CPC ......... *G01N 33/0075* (2013.01); *G08C 19/00* (2013.01); *H04L 29/02* (2013.01)

(58) Field of Classification Search
CPC ........................... G01N 33/0075; H04L 29/02
See application file for complete search history.

(56) References Cited

U.S. PATENT DOCUMENTS

| | | | |
|---|---|---|---|
| 2005/0088299 A1 | 4/2005 | Bandy et al. | |
| 2015/0163099 A1* | 6/2015 | Huang | H04W 28/0252 370/242 |
| 2017/0184558 A1 | 6/2017 | Berndt et al. | |

FOREIGN PATENT DOCUMENTS

| | | |
|---|---|---|
| DE | 102013008425 B3 | 5/2014 |
| DE | 102013111714 A1 | 4/2015 |
| DE | 102014015910 A1 | 5/2016 |
| WO | 2012139797 A1 | 10/2012 |

* cited by examiner

*Primary Examiner* — Benyam Haile
(74) *Attorney, Agent, or Firm* — McGlew and Tuttle, P.C.

(57) ABSTRACT

A checking unit as well as to a process are provided for checking a gas-measuring device. With the checking unit and process it is possible to efficiently detect measured gas values with a gas-measuring device.

20 Claims, 8 Drawing Sheets

CONTROL UNIT AND METHOD FOR CONTROLLING A GAS MEASURING DEVICE

CROSS REFERENCE TO RELATED APPLICATIONS

This application is a United States National Phase Application of International Application PCT/EP2018/077322, filed Oct. 8, 2018, and claims the benefit of priority under 35 U.S.C. § 119 of German Application 10 2017 009 525.6, filed Oct. 12, 2017, the entire contents of which are incorporated herein by reference.

TECHNICAL FIELD

The disclosure relates to a checking unit, for checking a gas-measuring device.

TECHNICAL BACKGROUND

Gas-measuring devices, which can detect different types of gaseous substances in an ambient air by means of different types of gas sensors, are known. A measured gas value obtained by means of a type of gas sensor relative to a certain or predefined type of gaseous substance may be displayed for a user, for example, on a display unit of the gas-measuring device.

Further, applications are known, in which, for example, a so-called measurement of safe levels shall be carried out in an industrial plant. A user detects in this case a measured gas value at a certain location of the industrial plant by means of a gas-measuring device. The goal is to determine whether a gas concentration of a predefined type of gaseous substances at the measuring location exceeds a critical value. The user can then read such a measured gas value, for example, from a display unit of the gas-measuring device and log it in different manners. A first possibility of logging would be to enter the corresponding measured gas value by hand in a log by means of a pen. After detecting different measured gas values at different measuring locations, the user can then transfer or file the log later at a central management or administration office of the industrial plant. Another possibility would be to enter this measured gas value into a mobile communication device in order to then transmit this measured gas value to the central management or administration office.

Such procedures for detecting different measured gas values at different gas-measuring locations may represent a complicated procedure depending on the number of measured values to be detected and on the number of measuring locations to be inspected.

Further, a user of a gas-measuring device can obtain information from the central management and administration office on the measuring locations at which he shall detect measured values on the types of gaseous substances he shall measure before visiting the different measuring locations.

SUMMARY

An object of the present invention is to provide a checking unit as well as a process for checking a gas-measuring device, by means of which unit and process it is possible to detect and to transmit measured gas values by means of a gas-measuring device in an efficient manner.

The checking unit according to the present invention for checking a gas-measuring device, having a first data interface, a second data interface as well as a control unit, comprises the control unit, which is configured to receive a first request message from a network unit via the first data interface, which said message indicates a request for providing at least one measured gas value of a predefined type of gaseous substance, further to transmit to the gas-measuring device via the second data interface a second request message, which has a request for sending information related to a potential presence of at least one type of gas sensor of the gas-measuring device, further to receive from the gas-measuring device via the second data interface a reply message, which has the information relating to the potential presence of the at least one type of gas sensor, further to derive from the information of the reply message whether a type of gas sensor that corresponds to the predefined type of gaseous substance is present in the gas-measuring device, as well as to send, in case of a positive derivation result, a third request message to the gas-measuring device, which indicates a request to transmit the at least one measured gas value of the predefined type of gaseous substance to the control unit, and to provide this at least one measured gas value to the network unit upon receipt of the at least one measured gas value.

It is possible by means of the checking unit according to the present invention to check automatically whether a gas-measuring device has a type of gas sensor that corresponds to a predefined type of gaseous substance from a request for detecting a measured gas value. In case a type of gas sensor that corresponds to the predefined type of gaseous substance is indeed present in the gas-measuring device, the gas-measuring device is prompted to transmit the measured gas value to the checking unit or to the control unit thereof by means of the third request message. It is consequently unnecessary for the gas-measuring device to permanently or continuously transmit measured values to the checking unit or to the control unit thereof, but a data transmission of measured values from the gas-measuring device to the checking unit or to the control unit thereof can be checked by means of the checking unit according to the present invention.

If, for example, the second data interface is a wireless interface, it may be advantageous if the gas-measuring device transmits the measured gas value to the checking unit or to the control unit thereof only when a measured gas value of the predefined type of gaseous substance can indeed be provided by the gas-measuring device. If a plurality of gas-measuring devices in a larger industrial plant provided measured values permanently via a communication network, for example, a wireless network, a case could arise in which the respective communication signals or wireless signals would mutually interfere with one another and thus needlessly utilize or burden network resources of the wireless network.

Consequently a network resource is burdened or utilized by the transmission of a measured gas value due to the present invention only in case a type of gas sensor corresponding to the type of gaseous substance is indeed present in the gas-measuring device.

Further, it is advantageous for the user that it is possible for him by means of the checking unit according to the present invention to be able to carry out a transmission of measured gas values to the network unit in such an automated manner that the network unit, which is located, for example, in a center or management center of the industrial plant must receive data only when the gas-measuring device is also indeed suitable for detecting and providing the measured gas value relative to the predefined type of gaseous substance.

Further, the checking unit according to the present invention is advantageous because the first reply message, which indicates a request for providing at least one measured gas value of a predefined type of gaseous substance, can be transmitted to the checking unit or to the control unit thereof already at a time at which the checking unit is not yet located in a sufficiently close proximity of the gas-measuring device in order to exchange messages with this by means of a wireless transmission. The checking unit can consequently receive at first only the first request message and it can then trigger the transmission of the measured value from the gas-measuring device to the checking unit by means of the second request message later, at a time at which a wireless communication between the checking unit and the gas-measuring device is possible via the second data interface. This may be advantageous especially when a data transmission via the second data interface is based on a type of wireless transmission that is only capable of transmitting wireless signals over shorter distances between the gas-measuring device and the checking unit. This may be the case, for example, in the case of a type of wireless transmission such as the Bluetooth standard. The gas-measuring device does not now have to establish a communication to the central network unit, which may be located, e.g., in the central management or administration unit. A user can rather bring the checking unit later to a sufficiently close proximity of the gas-measuring device in order to then receive the measured gas value from the gas-measuring device and to transmit it to the network unit via the first data interface, which possibly makes possible a communication over greater distances. The first data interface may make possible, e.g., a data transmission according to the LTE (Long-Term Evolution) standard.

Further, the checking unit according to the present invention is also advantageous in case the gas-measuring device is a gas-measuring device that can be carried by a user or can be transported by a user. This makes it possible that the checking unit will receive the first request message from the network unit initially via the first data interface, for example, at the location of a central management or administration office, e.g., via a wired or wireless data transmission, and that the user will bring both the portable checking unit and the portable gas-measuring device later, at a second time, to a location at which the measured gas value can be detected and provided by the gas-measuring device under the control of the checking unit. If a measured gas value was then detected by the checking unit with the use of the gas-measuring device, this value can then be transmitted later, at a third time, from the checking unit via the first data interface to the network unit, e.g., in a wireless manner via an LTE connection. This is especially advantageous when a data communication via the first data interface to the network unit is not possible based on a lack of wireless coverage. As a result, the user can then transmit the measured gas value to the network unit via the first data interface of the checking unit at the third time, when the checking unit is located at a location at which a data transmission by means of wireless transmission is again possible based on a sufficient wireless network coverage from the checking unit via the first data interface to the network unit.

Further, the checking unit according to the present invention is advantageous because the gas-measuring device itself does not have to make possible a wireless transmission via its own data interface to the network unit, but this can be made possible by the checking unit. As a result, the gas-measuring device can be limited to making possible a wireless transmission to the checking unit only via a wireless standard, which can transmit data over shorter distances only, for example, the Bluetooth standard. The gas-measuring device does not have to make possible itself a wireless transmission ever longer distances, as, for example, in the case of an LTE connection, and therefore it also does not have to be registered with a registration of its own, for example, by means of an LTE SIM card, as an individual user in a mobile network. In other words, it is consequently possible that the checking unit has a sufficient wireless transmission over greater distances and this does not have to be guaranteed by the gas-measuring device.

The checking unit can now be brought, for example, in the form of a unit that can be carried by a user, to different locations with respective different gas-measuring devices in order to then transmit respective measured gas values of the respective gas-measuring devices to the network unit.

The checking unit is preferably configured to be such that the second request message has a request for sending configuration information, which indicates gas sensor types that are indeed present in the gas-measuring device, wherein the reply message has the configuration information and wherein the control unit derives from the predefined type of gaseous substance and from the configuration information whether a type of gas sensor corresponding to the predefined type of gaseous substance is present in the gas-measuring device.

The checking unit is preferably configured such that the second request message has information that indicates the predefined type of gaseous substance or a type of gas sensor corresponding to the predefined type of gaseous substance, the request message having information that indicates whether a type of gas sensor corresponding to the predefined type of gaseous substance is present in the gas-measuring device, and the control unit deriving from the information of the reply message whether a type of gas sensor that corresponds to the predefined type of gaseous substance is present in the gas-measuring device.

The checking unit is preferably configured such that the control unit is configured to send the third request message via the second data interface to the gas-measuring device in case a type of gas sensor that corresponds to the predefined type of gaseous substance is present in the gas-measuring device, further to receive the at least one data message of the first type via the second data interface, as well as to transmit a data message of the second type, which indicates the at least one measured gas value of the predefined type of gaseous substance, to the network unit via the first data interface upon receipt of the at least one data message.

The checking unit is preferably configured such that the third request message further indicates a request for detecting the at least one measured gas value of the predefined type of gaseous substance by the gas-measuring device.

The checking unit is preferably configured such that the checking unit further has a user interface and wherein the control unit is further configured to transmit the data message of the second type via the first data interface to the network unit as a function of an input of a user into the user interface.

The checking unit is preferably configured such that the checking unit further has an optical display unit, wherein the control unit is further configured to receive via the second data interface a plurality of data messages of the first type, which indicate a plurality of measured gas values, further to select from the plurality of measured gas values a current measured gas value as well as at least one additional measured gas value and to output them for the user by means of the optical display unit, as well as further to select one of the outputted measured gas values as a function of a user input of the user into the user interface and to transmit it as the at least one measured gas value of the predefined type of gaseous substance to the network unit by means of the data message of the second type.

The checking unit is preferably configured such that the control unit is further configured to generate a measured value data set on the basis of the at least one measured gas value, further to receive a predefined value data set, further to generate a digital signature of the at least one measured value data set on the basis of the predefined value data set and of the at least one measured value data set as well as further to transmit the at least one measured gas value of the predefined type of gaseous substance in the form of the measured value data set and of the digital signature to the network unit by means of the data message of the second type.

The checking unit is preferably configured such that the control unit is further configured to transmit an information message, which indicates that the at least one measured gas value of the predefined type of gaseous substance cannot be provided, to the network unit via the second data interface in case a type of gas sensor corresponding to the predefined type of gaseous substance is not present in the gas-measuring device.

The checking unit is preferably configured such that the control unit is further configured to determine the measured gas value of the predefined type of gaseous substance on the basis of a user input into the user interface in case a type of gas sensor corresponding to the predefined type of gaseous substance is not present in the gas-measuring device and to transmit it to the network unit by means of the data message.

The checking unit is preferably configured such that the control unit is further configured to bring about a data exchange with the gas-measuring device via the second data interface for bringing about a logical data transmission coupling between the checking unit and the gas-measuring device, as well as further to bring about a data exchange with an additional gas-measuring device via the second data interface in case no type of gas sensor corresponding to the predefined type of gaseous substance is present in the gas-measuring device to bring about a further logical data transmission coupling between the checking unit and the additional gas-measuring device, as well as further to derive by means of a data exchange with the additional gas-measuring device via the second data interface whether a type of gas sensor that corresponds to the predefined type of gaseous substance is present in the additional gas-measuring device, as well as to send the third request message to the additional gas-measuring device in the case of a positive result of derivation, and to make this at least one measured gas value available to the network unit upon receipt of the at least one measured gas value of the predefined type of gaseous substance.

Further, a process for checking a gas-measuring device with the following steps provided:
reception of a first request message from a network unit via a first data interface, wherein the first request message indicates a request for detecting at least one measured gas value of a predefined type of gaseous substance,
further, transmission of a second request message to the gas-measuring device via a second data interface, wherein the second request message has a request for sending information related to the potential presence of at least one type of gas sensor of the gas-measuring device,
further, reception of a reply message from the gas-measuring device via the second data interface, wherein the reply message has the information concerning the potential presence of the type of gas sensor,
based on the information of the reply message, derivation of whether a type of gas sensor, which corresponds to the predefined type of gaseous substance, is present in the gas-measuring device, and, in the case of a positive result of the derivation,
Sending of a third request message to the gas-measuring device, which indicates a request to transmit the at least one measured gas value of the predefined type of gaseous substance to the checking unit, and
provision of the at least one measured gas value to the network unit upon receipt of the at least one measured gas value.

The checking unit being proposed may be considered to be a device. Further, the control unit may be in the form of a computer. Therefore, a device with a computer, which is configured to carry out the process being proposed, is further proposed.

Further, a computer program with a program code for carrying out the process being proposed when the program code is executed on a computer, a processor or a programmable hardware component is proposed.

The present invention will be explained in more detail below on the basis of special embodiments without limitation of the general inventive idea on the basis of the figures.

The exemplary embodiments shall not be considered to represent a limitation of the present invention. Rather, variations and modifications, especially such variants and combinations which the person skilled in the art can find in respect to accomplishing the object, for example, by a combination or variation of individual features contained in the general or special text of the description as well in the claims and/or in the drawings and lead to a new subject by combinable features, are possible within the framework of the present disclosure. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1A:
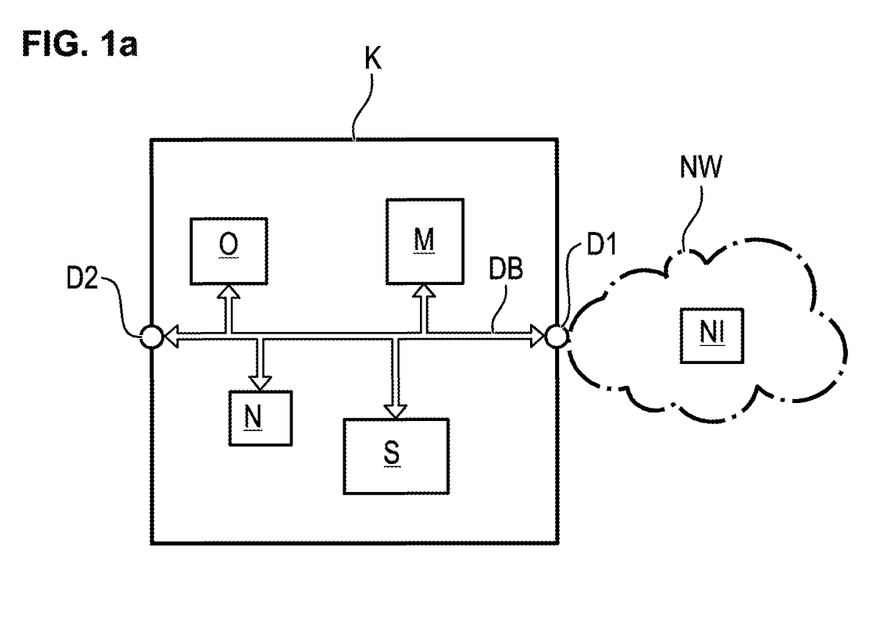
FIG. 1a is a schematic view of a preferred embodiment of the checking unit according to the present invention.

Referring to the drawings, FIG. 1*a* shows a preferred embodiment of the checking unit K according to the present invention. The checking unit K has a first data interface D1 as well as a second data interface D2 and a control unit S.

The checking unit K further has preferably a memory unit M. The data interfaces D1, D2 as well as the control unit S as well as the memory unit M are preferably connected to one another via an internal data bus DB.

The control unit S may be in the form of hardware and/or software.

The checking unit K may communicate with a central network unit NI via a network NW via the data interface D1.

The checking unit K from FIG. 1*a* preferably has, furthermore, a user interface N for detecting a user input. The user interface N is connected, just like other partial units of the checking unit K, to the other partial units by means of the data bus DB.

The checking unit K preferably has an optical display unit O, which is connected to the other partial units of the checking unit K via the data bus DB.

The user interface N and the optical display unit O may also be configured as an integral unit, e.g., in the form of a touch-sensitive display unit, which may preferably be called a touch screen.

Figure 1B:
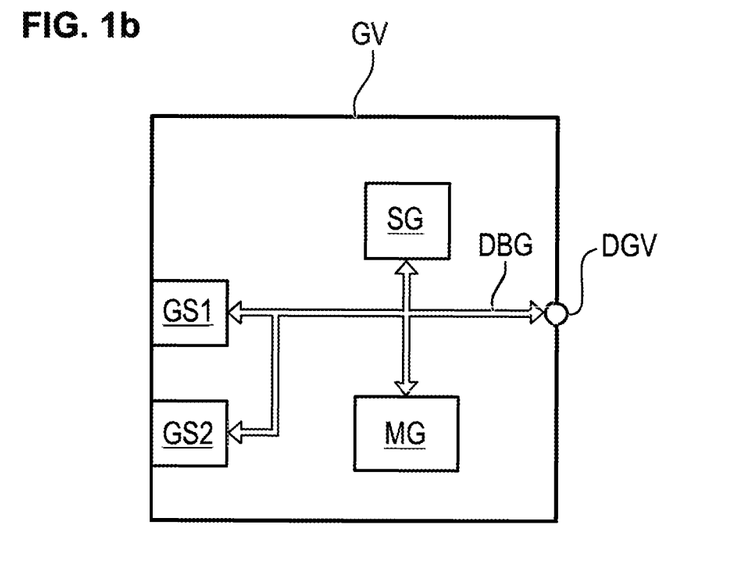
FIG. 1b is a schematic view of a gas-measuring device.

FIG. 1*b* shows a gas-measuring device GV, which can communicate in terms of data technology with the data interface D2 of the checking unit K by means of a data interface DGV. The gas-measuring device GV preferably has a control unit SG as well as a memory unit MG. The gas-measuring device has at least one type of gas sensor GS1, GS2. The at least one type of gas sensor GS1, GS2, the data interface DGV, the control unit SG and the memory unit MG are preferably connected to one another via an internal data bus DBG.

The gas-measuring device GV has two different gas sensor types GS1, GS2 in this exemplary embodiment. A gas sensor type is a certain gas sensor, which is suitable for detecting measured gas values relative to a predefined type of gaseous substance. One example of a type of gaseous substance is carbon monoxide. Another example of a type of gaseous substance is hydrogen sulfide. Yet another example of a type of gaseous substance is methane.

It may be necessary in a gas-measuring device GV that a certain type of gas sensor also be present for detecting a predefined type of gaseous substance. Not all gas sensor types GS1, GS2 are possibly suitable for all kinds of gaseous substance types.

A situation may therefore possibly develop in which a user would like to use a gas-measuring device GV in order to detect a measured gas value relative to a predefined type of gaseous substance, but it may not possibly be clear for the user before the step of detection whether the gas-measuring device GV has an adequate type of gas sensor for the certain or predefined type of gaseous substance.

Figure 2A:
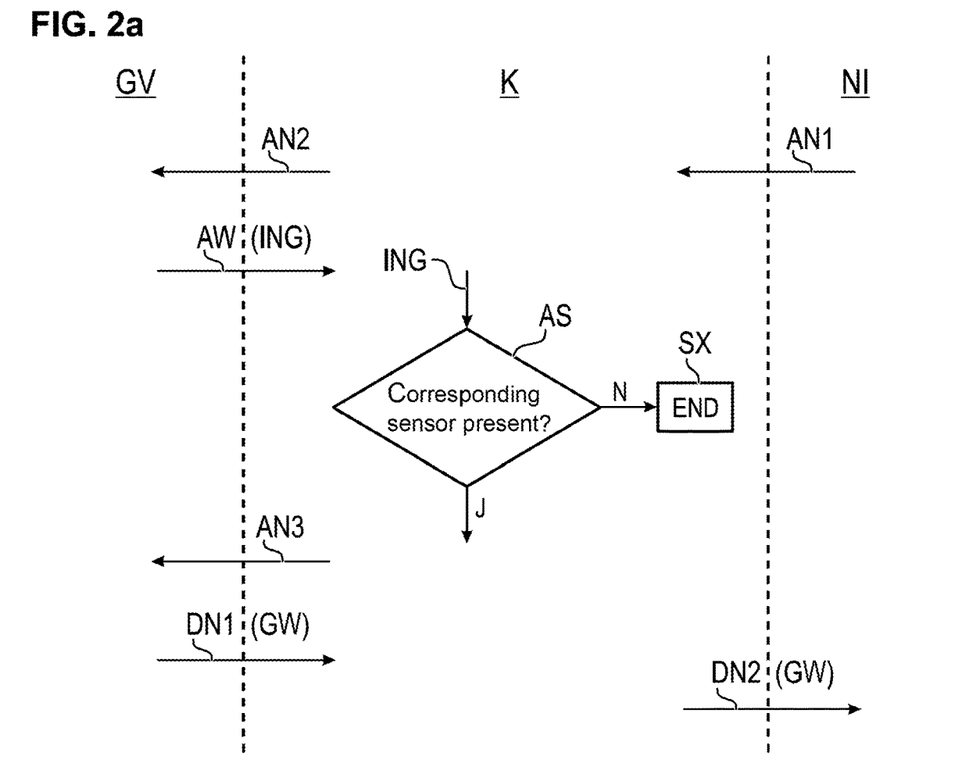
FIG. 2a is a view showing an exchange of messages.
Figure 3A:
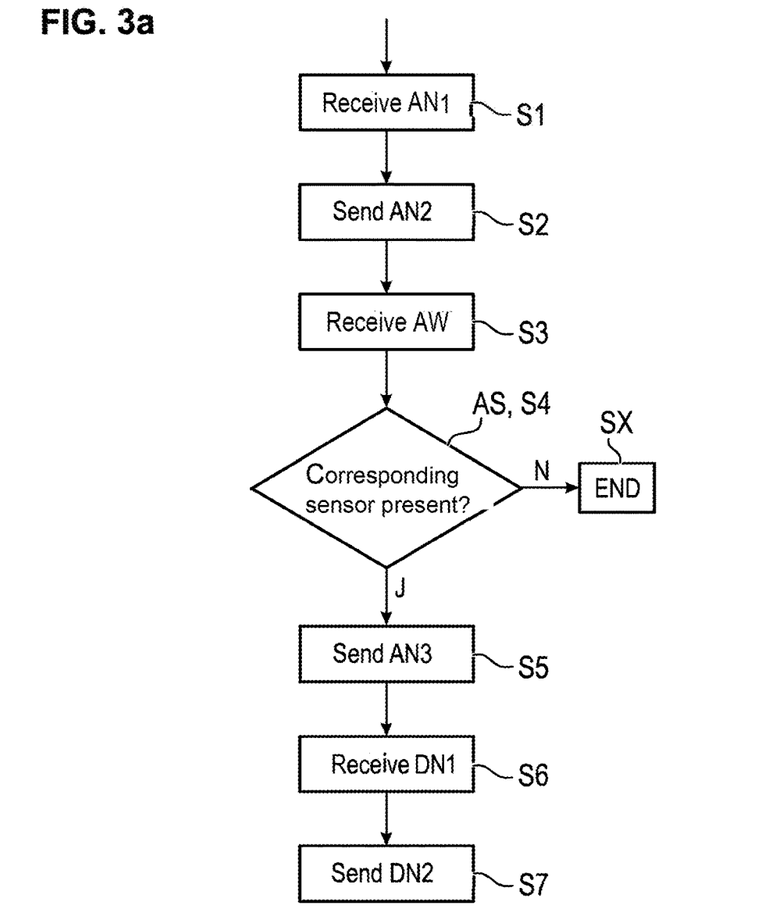
FIG. 3a is a flow diagram showing process steps for carrying out the process according to the present invention.

A checking unit according to the present invention, which will be explained below in more detail as an example on the basis of an exchange of data messages according to FIG. 2*a* as well as of a sequence of process steps according to FIG. 3*a*, is therefore proposed. FIG. 2*a* as well as 3*a* shall be considered here together within the framework of the following explanation.

A request message AN1 is sent from a central network unit NI to the checking unit K. The control unit of the checking unit K receives the first request message AN1 in step S1 via the first data interface.

This request message AN1 contains data elements that indicate that at least one measured gas value shall be provided in relation to a certain or predefined type of gaseous substance.

For example, the first request message AN1 indicates that hydrogen sulfide shall be measured. The request message AN1 preferably indicates, further, the location at which the measured gas value shall be detected. This may be indicated, for example, by the request message AN1 indicating exactly the gas-measuring device that shall be used to detect the measured gas value; for example, the network unit NI knows a fixed location of the gas-measuring device GV.

Information can then be outputted for the user, for example, on the basis of the request message AN1 by the control unit on the optical display unit as to the location and the particular gas-measuring device at which and by means of which he shall detect and provide a measured gas value of a certain or predefined type of gaseous substance by means of a gas-measuring device.

According to FIGS. 2*a* and 3*a*, the control unit then sends a second request message AN2 to the gas-measuring device via the second data interface in a step S2. The request message AN2 indicates a request for sending information ING by the gas-measuring device. The information ING is related to a potential presence of at least one gas sensor type of the gas-measuring device GV.

The control unit consequently prompts the gas-measuring device to provide information, which is in connection with gas sensor types present in the gas-measuring device GV.

The control unit then receives in a step S3 a reply message AW via the second data interface from the gas-measuring device GV. The reply message AW contains the information ING, which is related to a potential presence of at least one gas sensor type. The reception of the reply message AW takes place in a process step S3.

In a derivation step AS or S4, the control unit then derives from the information ING of the reply message AW whether a gas sensor type that corresponds to the predefined type of gaseous substance, which was predefined by the first request message, is present in the gas-measuring device GV.

If the result of this derivation or checking is negative, i.e., no gas sensor type that corresponds to the predefined type of gaseous substance is present in the gas-measuring device GV, the process branches off further to a process step SX, in which the process preferably ends.

If the result of the derivation or checking is positive, i.e., a gas sensor type that corresponds to the predefined type of gaseous substance is present in the gas-measuring device, the control unit S sends in process step S5 a third request message AN3 via the second data interface D2 to the gas-measuring device GV. The third request message AN3 indicates a request for transmitting the at least one measured gas value of the predefined type of gaseous substance to the control unit. Consequently, the gas-measuring device is prompted hereby to send or transmit the at least one measured gas value to the control unit or to the checking unit K.

If a data message of the first type, DN1, which contains the measured gas value GW, is then received in a step S6, the control unit then sends in a step S7 the at least one measured gas value in the form of a data message of the second type DN2 to the network unit NI.

As was already explained above, the checking unit according to the present invention and the process according to the present invention are advantageous because they eliminate the need for the gas-measuring device GV to have to transmit data messages with the measured gas value GW permanently or continuously over time to the checking unit K or to the data interface D2 thereof, but a data technological transmission from the gas-measuring device GV to the checking unit or to the control unit thereof takes place only when it is indeed clear that the gas-measuring device GV can indeed provide measured gas values, which are of the kind of the predefined type of gaseous substance.

The second data interface is preferably a wireless data interface in the form of a wireless interface according to a wireless standard, for example, Bluetooth, WLAN, WiFi or of another type.

It is consequently possible as a result that the checking unit is, for example, a device, which can be carried by a user or even held in the hand, and by means of which the controlled and above-described detection of measured gas values is possible, without the user having to hold the gas-measuring device in the hand. The gas-measuring device may consequently be a module with a housing of its own, separate from the checking unit.

Further, it is possible that the gas-measuring device may already be present at the location of the measurement, but the user with his checking unit needs only to arrive at the location of the measurement later. This is advantageous precisely in industrial plants, because, for example, gas-measuring devices may be installed permanently or semi-permanently in this case, but the user needs only to carry with him his checking unit to detect different measured gas values of different types of gaseous substances at different measuring locations and he can ascertain by means of the checking unit according to the present invention that a detection of a measured gas value relative to a predefined type of gaseous substance, which is requested by the network unit, is indeed possible by means of the gas-measuring device currently being used or addressed. It may happen, for example, that the network unit predefines a request to the checking unit, in which a detection of a measured gas value of a certain or predefined type of gaseous substance is requested, but there is an administrative error in such a form that the network unit assumes the predefined types of gaseous substance to be able to be measured by a certain gas-measuring device, but the gas-measuring device has no corresponding gas sensor for the predefined types of gaseous substances at all. Such an erroneous assumption can be eliminated by the checking unit according to the present invention and by the process according to the present invention, because the transmission of a measured gas value takes place only after checking the gas sensor types of the gas-measuring device.

The first data interface may preferably be a wireless interface, for example, in the form of a mobile wireless interface according to the LTE standard. It is then possible as a result that the user can use the checking unit for the data communication with the network unit over greater distances, while it is possible at the same time that the gas-measuring device makes possible only a wireless data communication over shorter distances via its data interface to the second data interface of the checking unit, such as in the case of, for example, Bluetooth or WLAN. As a result, the user can consequently use the checking unit to make possible a data transmission by means of different wireless standards to transmit the measured gas value, without the gas-measuring device itself having to make possible a data communication in the form of a wireless connection over greater distances, e.g., an LTE wireless connection, to the network unit.

However, the first data interface may preferably also be a wired data interface, for example, a USB (Universal Serial Bus) interface, via which the first request message AN1 can then be transmitted to the checking unit or the control unit. This may be advantageous, for example, in a scenario in which a user connects his checking unit via the first data interface, e.g., by means of a USB docking station, to the network unit at the beginning of a work shift in an industrial plant, and the network unit can transmit right then the first request message AN1 to the checking unit via the USB connection. The user can then receive, e.g., more than a first request message and receive as a result a plurality of requests for detecting different measured gas values of different types of gaseous substances at different locations. At a later time, the user can then bring the checking unit into the vicinity of respective gas-measuring devices at respective measuring locations in order to obtain measured gas values in the above-described manner from the respective gas-measuring devices and to transmit them to the central network unit.

Figure 2B:
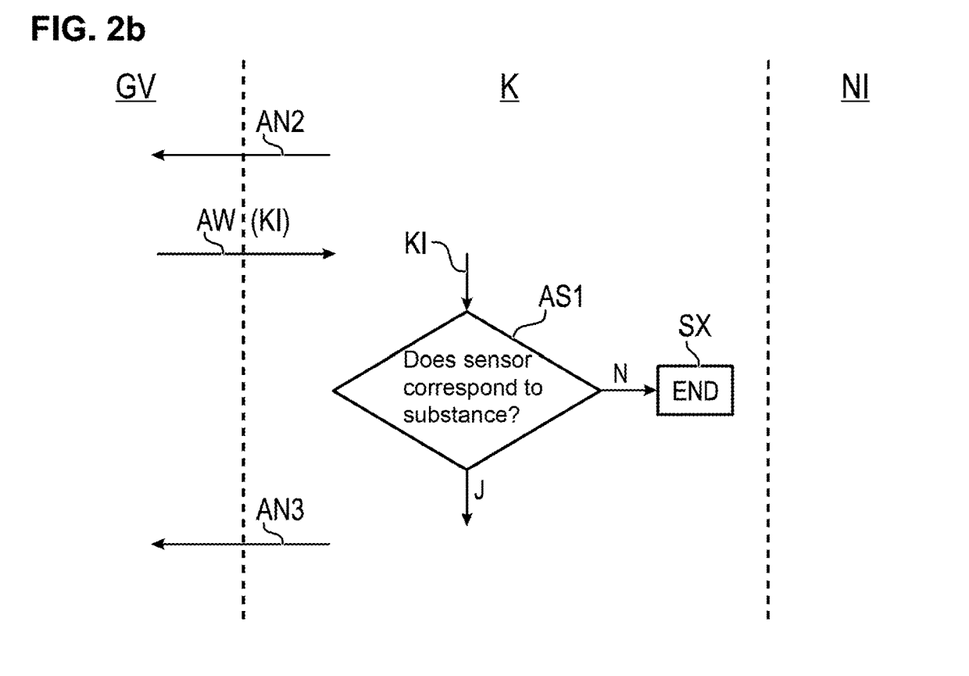
FIG. 2b is a view showing an exchange of messages.

FIG. 2b shows a first variant, in which the control unit S derives whether a gas sensor type, which corresponds to the predefined type of gaseous substance, is present in the gas-measuring device GV. According to this first variant, the request message AN2 has a request to the gas-measuring device for sending configuration information KI from the gas-measuring device to the control unit or to the checking unit. This configuration information KI, which the control unit or the checking unit requests from the gas-measuring device GV, will then indeed indicate gas sensor types GS1, GS2 present in the gas-measuring device GV. The reply message AW then has this configuration information KI. The configuration information KI informs the checking unit K or the control unit thereof on which gas sensor types GS1, GS2 are present in the gas-measuring device GV.

This configuration information KI is used in a variant of a derivation step AS1 to derive whether a gas sensor type corresponding to the predefined type of gaseous substance is present in the gas-measuring device GV. It shall be assumed in this example that the type of gaseous substance predefined via the request message AN1 is a type to which the gas sensor type GS1 of the gas-measuring device GV corresponds.

The process then branches off in this case further to step S5 from FIG. 3a, in which the third request message AN3 is then sent to the gas-measuring device GV. The process then proceeds according to the manner described above with reference to FIGS. 2a and 3a.

In this first variant of the derivation or of the derivation step AS1, the control unit of the checking unit K will consequently make the decision on sending the request message AN3. The control unit does this based on the fact that the control unit itself compares the predefined type of gaseous substance with information or the configuration information KI, which provides information precisely on which gas sensor types GS1, GS2 are present in the gas-measuring device GV. The essential logic consequently lies in the first variant of the derivation in the control unit of the checking unit K.

Figure 2C:
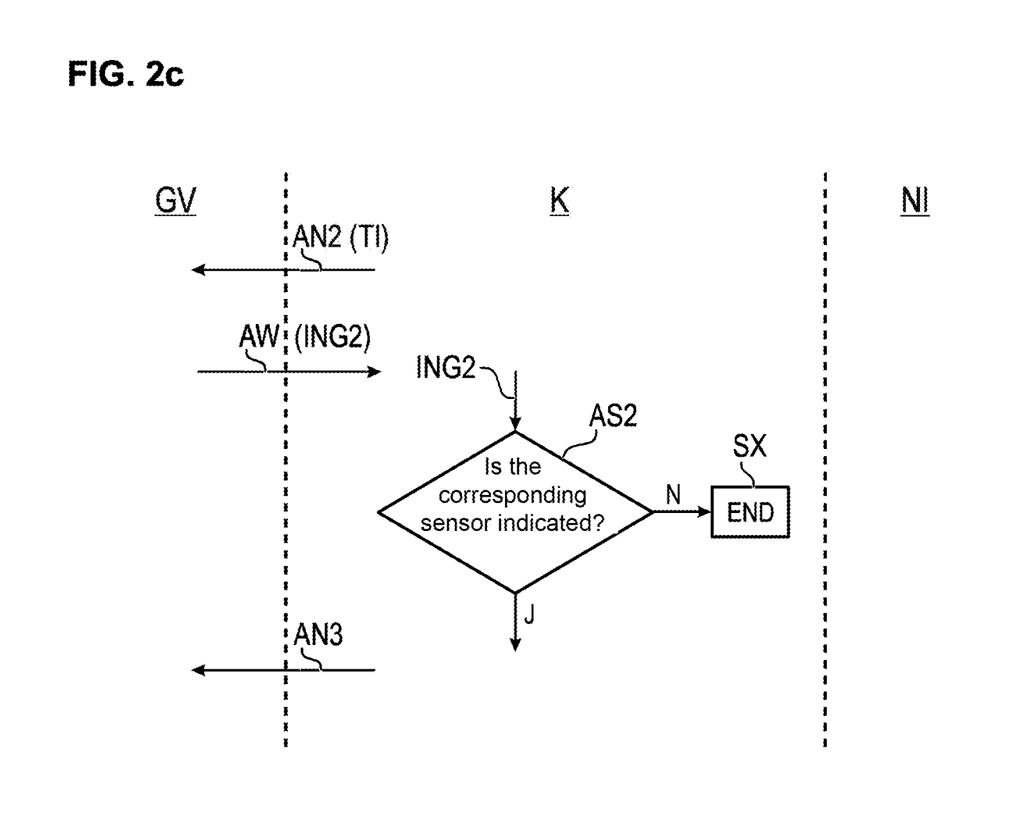
FIG. 2c is a view showing an exchange of messages.

FIG. 2c shows a second variant of the derivation or of the derivation step AS2 for deriving or for determining whether a gas sensor type that corresponds to the predefined type of gaseous substance is present in the gas-measuring device GV. According to this second variant, the second request message AN2 has information TI that indicates the predefined type of gaseous substance or a gas sensor type corresponding to the predefined type of gaseous substance.

The control unit S can consequently transmit now a data element as information TI to the gas-measuring device GV by means of the request message AN2, which data element indicates the kind of gaseous substance type for which a measured gas value shall be detected. As an alternative, the control unit S may provide as the information TI in the second request message AN2 a data element which indicates a gas sensor type corresponding to the predefined type of gaseous substance. A gas sensor type may be characterized in terms of data technology, for example, by the presence of a certain type number of a gas sensor type as the information TI in the second request message AN2.

In this second variant, the reply message AW has information ING2, which indicates whether a gas sensor type corresponding to the predefined type of gaseous substance is present in the gas-measuring device.

This information ING2 may be, for example, a simple Boolean data element in the form of a 0 or 1, wherein a 0 indicates, for example, that there is no corresponding gas sensor type in the gas-measuring device for the predefined type of gaseous substance.

The main logic of the determination of whether a gas sensor type corresponding to the predefined type of gaseous substance is available in the gas-measuring device is consequently on the side of the gas-measuring device in the second variant of the derivation. The control unit determines in the derivation step AS2 whether the data element or the information ING2 indicates that there is a gas sensor type that corresponds to the predefined type of gaseous substance in the gas-measuring device. If so, the process continues in this second variant with step S5 from FIG. 3a, in which the third request message is then transmitted to the gas-measuring device, as it was described before with reference to FIGS. 2a and 3a. In summary, it can be stated that the control unit consequently derives in this second variant from the information ING2 of the reply message whether a type of gas sensor that corresponds to the predefined type of gaseous substance is present in the gas-measuring device.

The third request message preferably indicates a request for detecting the at least one measured gas value of the predefined type of gaseous substance by the gas-measuring device. This configuration is advantageous because it is made possible hereby that the gas-measuring device GV from FIG. 1b does not have to detect measured gas values continuously or permanently by means of one or more gas sensor types GS1, GS2, but it must perform this only at the time at which the checking unit K from FIG. 1a or the control unit S thereof has determined that the gas-measuring device GV also has, indeed, a gas sensor type GS1 that corresponds to a predefined gaseous substance or to a predefined type of gaseous substance from the first request message. It is made possible hereby that the gas-measuring device can save energy for the purpose of non-permanent or non-continuous measured value detection.

In other words, the checking unit K according to the present invention is advantageous because a data transmission from the gas-measuring device G to the checking unit K has to take place only in case a measured gas value for the predefined type of gaseous substance can indeed be detected by means of the gas-measuring device and because a data transmission of measured gas values does not consequently have to take place continuously. Energy can be saved hereby in the gas-measuring device for the purpose of a data transmission of measured gas values.

Figure 3B:
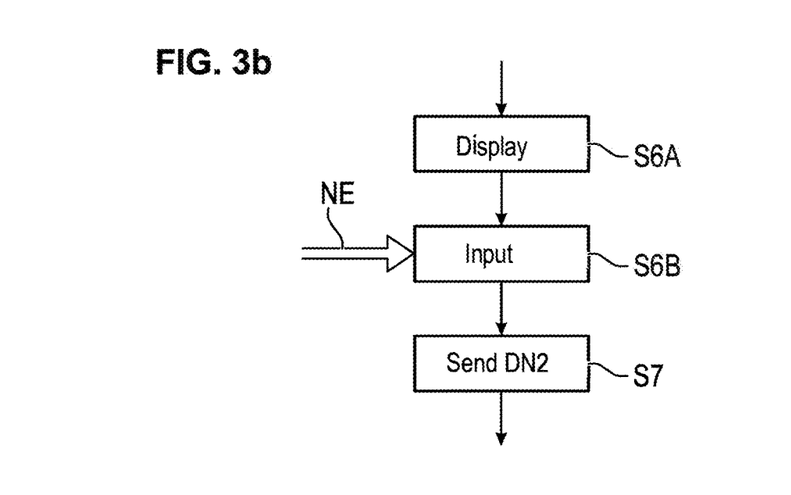
FIG. 3b is a flow diagram showing process steps for carrying out the process according to the present invention.

As was explained before with reference to FIG. 1a, the checking unit may preferably have a user interface, via which user inputs can be received. The control unit S can consequently display now, for example, a measured value GW via the optical display unit O for the user. The user has now the possibility of taking the measured value into account himself and to make, for example, a decision concerning the plausibility of the measured value. As is shown according to FIG. 3b, process step S6 from FIG. 3a may be followed by the process step S6A, in which this display takes place. In a subsequent step S6B, an input NE of the user can then be received, and the measured value GW can be transmitted by means of the data message of the second type DN2 to the network unit NI only after the presence of this input NE in process step S7. The user can consequently check by means of inputting or not inputting his user input NE whether the measured value is indeed transmitted by means of the data message of the second type DN2 to the network unit NI.

Figure 4A:
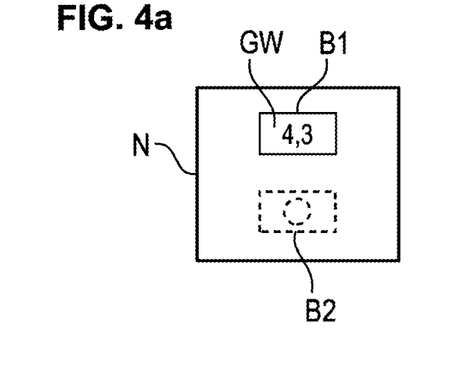
FIG. 4a is a schematic view of a preferred embodiment of a user interface N.

FIG. 4a, which shows a preferred embodiment of the user interface N, can be considered in connection with this. This embodiment of the user interface N preferably also represents at the same time the optical display unit O from FIG. 1a of the checking unit K as an integral partial device. The user interface N is a touch-sensitive display unit in this case, which may also be called touch screen.

By means of the user interface N, the control unit displays in a predefined display area B1 the measured gas value GW, which is a measured value of 4.3 in this example. The user can then enter, for example, the above-mentioned user input NE by touching the predefined area B1 in order to confirm the measured value GW being shown there.

As an alternative, another predefined display area B2, which is indicated by broken lines here, may be displayed at the user interface N, in which case a touching of the additional predefined display area B2 represents the above-described user input NE. Consequently, a user can now actuate, for example, a so-called touch button in order to trigger the transmission of the measured gas value GW by means of the data message of the second type DN2.

Figure 4B:
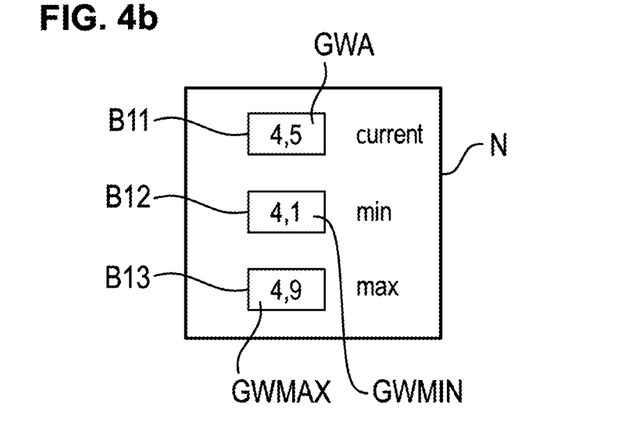
FIG. 4b is a schematic view of a preferred embodiment of a user interface N.
Figure 5:
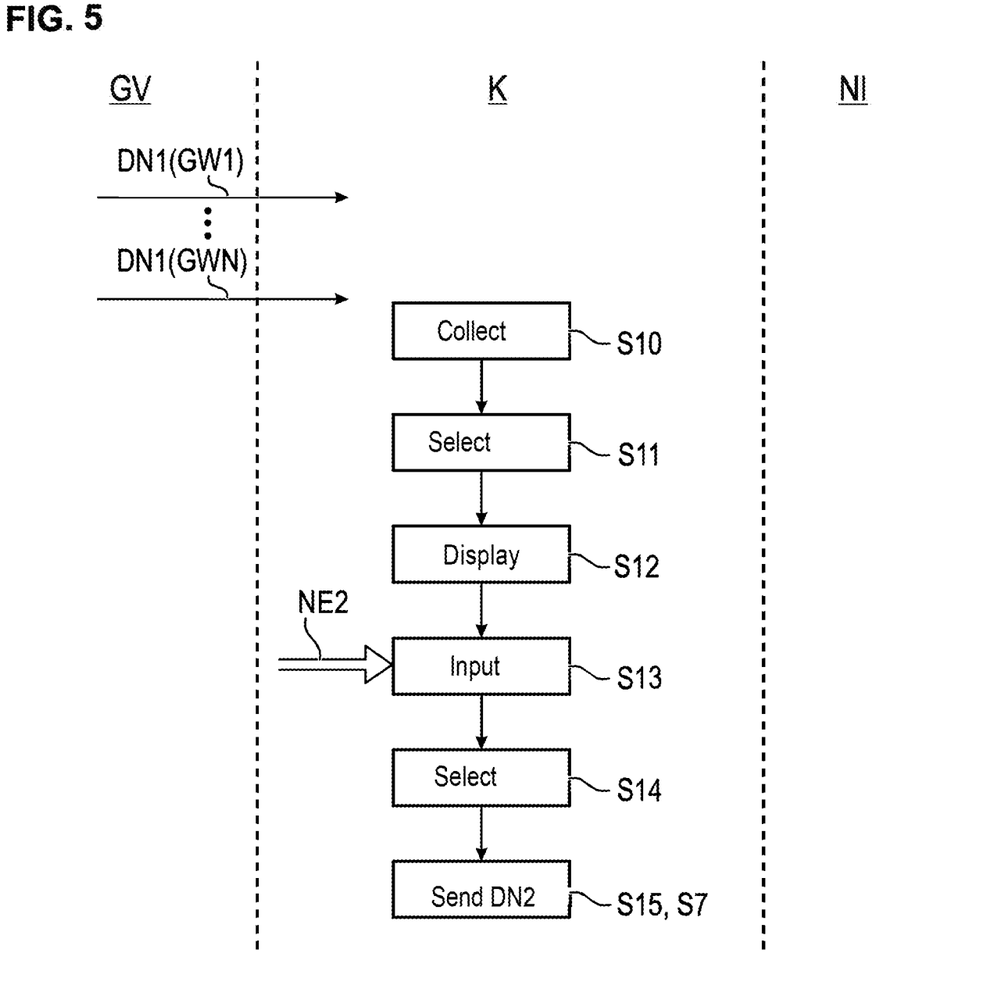
FIG. 5 is a view of a preferred process steps for selecting measured values.

FIG. 4b shows another preferred embodiment of the user interface N, which includes the optical display unit O from FIG. 1a as an integral partial device here as well. FIG. 5 shows preferred process steps, which will be explained now in more detail in connection with the representation of the user interface N from FIG. 4b.

The control unit of the checking unit can receive via the second data interface D2 a plurality of data messages of the first type DN1, which will then indicate a plurality of measured gas values GW1, . . . , GWN. Such a configuration of the process is advantageous, for example, when this plurality of measured gas values shall be analyzed by the control unit of the checking unit by means of continuous measured value detection by the gas-measuring device.

In a process step S10, the control unit then collects and stores, preferably by means of the memory unit, the plurality of measured gas values GW1, . . . , GWN. In a step S11, the control unit S then selects from the plurality of measured gas values GW1, . . . , GWN a current measured gas value GWA, which is shown in FIG. 4b in a predefined display area B11. Further, the control unit selects and stores at least one additional measured gas value GWMIN, which is displayed in FIG. 4b in a predefined display area B12. Further, a second additional measured gas value GWMAX may also be displayed or outputted as the highest measured gas value in an additional predefined display area B13. This display is represented by the process step S12 in FIG. 5. The selected measured gas values are consequently outputted to the user by means of a user interface or an optical display unit.

This embodiment of the process may be advantageous if the user himself shall have the power of decision on whether a current measured gas value GWA or else another measured gas value, such as a minimum or maximum measured gas value GWMIN, GWMAX, shall be transmitted as the measured gas value to the network unit. The user will consequently make another user input NE2 in the user interface in step S13 according to FIG. 5 in order to select the displayed or outputted measured gas value GWA, GWMAX, GWMIN. This may happen, for example, by the user touching one of the predefined display areas B11, B12, B13 from FIG. 4b as touch-sensitive display areas of the user interface N. The user selects hereby the measured gas value to be transmitted to the network unit.

The selected measured gas value is then transmitted to the network unit as the at least one measured gas value of the predefined type of gaseous substance by means of the data message of the second type DN2.

Figure 6:
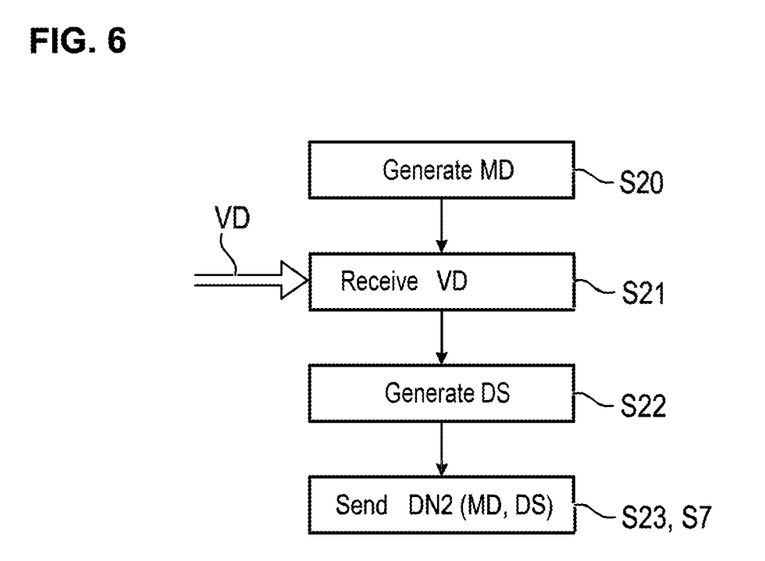
FIG. 6 is a flow diagram of a preferred process steps for generating signature data.

FIG. 6 shows preferred steps in connection with the generation of a digital signature.

It may be of interest for the network unit whether a measured gas value transmitted to it by the checking unit was indeed transmitted by such a checking unit that is trustworthy for the network unit. It may likewise be taken into account whether the user of the checking unit himself is trustworthy for the network unit.

The detection of measured gas values in industrial plants is a safety-critical checking procedure, in which errors of measurement or incorrectly detected measured values may have serious consequences. Further, it is necessary for operators of industrial plants for legal reasons or for reasons dictated by insurance laws to have the ability to demonstrate that the detection of measured gas values was carried out properly at different locations, for example, for the so-called measurement of safe levels. The measured values may be stored in such a case, and it may possibly have to be demonstrated later that this detection of the measured values was performed by proper users or else very specific checking units were used to detect the measured values.

It is therefore proposed that according to step S20 from FIG. 6, the control unit generate on the basis of the at least one measured gas value a measured value data set MD, which may be achieved, for example, by representing a measured value according to a predefined numeric coding. A predefined numeric coding is, for example, the ASCII code.

The control unit S can then receive a predefined value data set, for example, from the memory unit M according to FIG. 1a. This predefined value data set may be, for example, a so-called private key of a coding method. The control unit S may preferably receive this predefined value data set via the user interface N and then store it in the memory unit M. It becomes possible as a result that a user himself will predefine the secret or private key and that this code does not have to be linked permanently with the checking unit K or the control unit M thereof.

If the secret key or private key is stored permanently in the memory unit M, the measured value GW becomes linked hereby with the checking unit K or the control unit M thereof, which makes it possible to demonstrate later that the measured value GW was transmitted such that it was detected by or by means of a special checking unit K.

If, by contrast, provisions are made for entering the private key by means of the user interface N by the user, it can then be possible to demonstrate later that a certain user, who had knowledge of this private key, was responsible for the detection and the transmission of the measured value to the network unit.

The reception of the predefined value data set VD is represented according to FIG. 6 by the process step S21.

According to a digital signature process, the control unit can then generate a digital signature DS of the at least one measured value data set on the basis of the predefined value data set, i.e., of a private key, and of the at least one measured value data set.

If the measured value data set is then stored together with the data set of the digital signature, for example, in the central network unit, it will also be possible to demonstrate later whether a certain user or else a certain device was involved in the detection of the measured value, which is represented by the measured value data set.

According to step S23, which corresponds to step S7 from FIG. 3a, the second data message or data message of the second type DN2 is then transmitted to the network unit NI, which has the measured value data set MD and the digital signature DS in this example.

According to FIGS. 2a, 2b, 2c, it can be decided in the respective derivation steps AS, S1, S2 that no gas sensor type that corresponds to the predefined type of gaseous substance is present in the gas-measuring device. According to the exemplary embodiment explained there, the process can then be branched off to a process step SX, in which the process preferably ends.

Figure 7A:
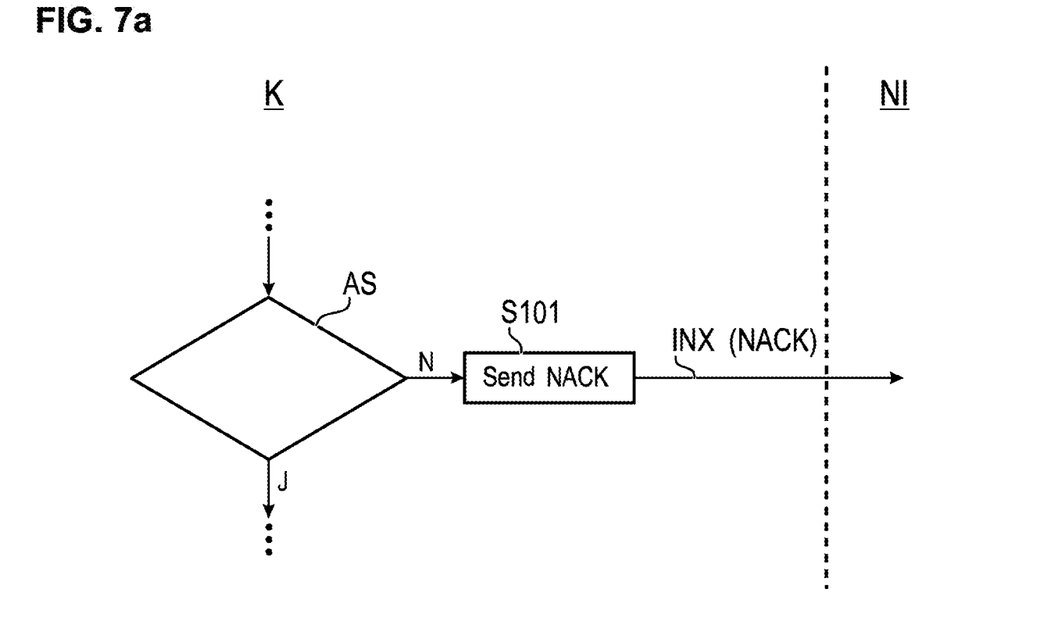
FIG. 7*a* is a view showing preferred process steps for informing a central network unit.

According to the exemplary embodiment shown in FIG. 7a, the process may be branched, as an alternative, to a process step S101, in which an information message INX is then transmitted to the network unit NI, rather than to a process step SX.

The information message INX then indicates that the at least one measured gas value of the predefined type of gaseous substance cannot be provided. This is advantageous because the network unit NI is informed in case the gas-measuring device has no gas sensor type that corresponds to the predefined type of gaseous substance, and it can derive corresponding steps itself.

Figure 7B:
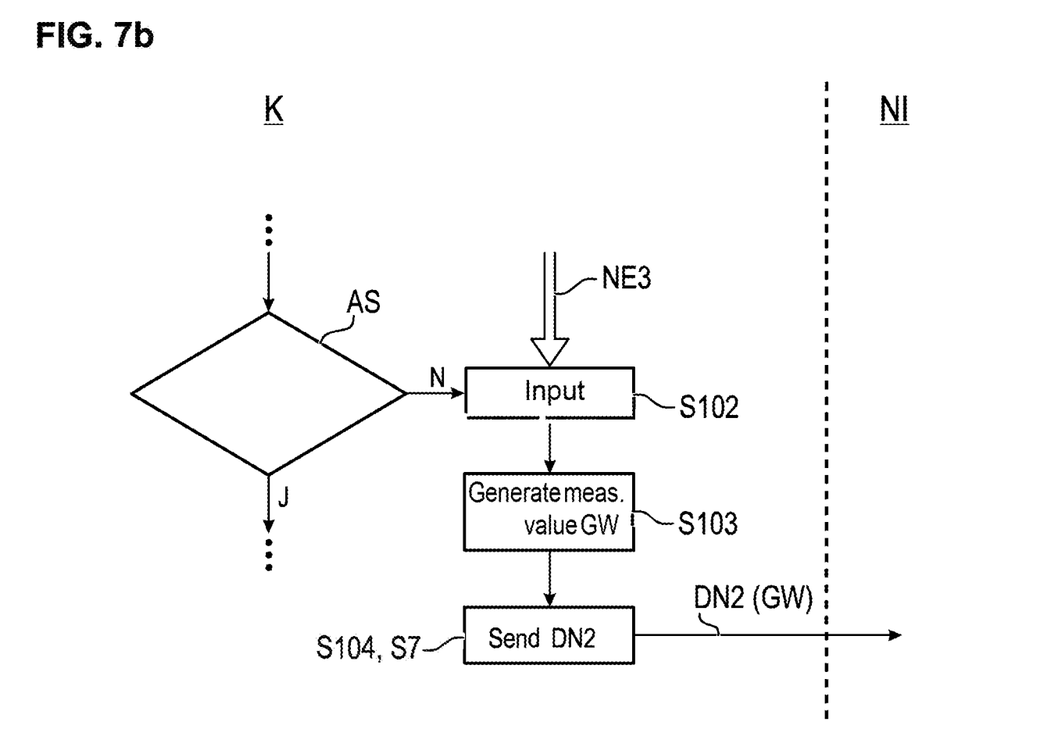
FIG. 7*b* is a view showing preferred process steps for detecting a measured value by means of a user input.

According to FIG. 7b, provisions can be made after the derivation step AS in case no gas sensor type that corresponds to the predefined type of gaseous substance is present in the gas-measuring device for the user to enter a measured gas value himself by means of a user interface and for this to be used then instead of a gas value transmitted to the data interface D2.

Consequently, a user input NE3 of a user can then be received in a process step S102. The user input may be effected here, for example, via a touch-sensitive display unit N, for example, a touch screen, in which case fields for presetting measured values, which the user can use, are then displayed on the display unit or user interface. As an alternative, the user interface may also be a keyboard or another unit for inputting a user input.

Based on the user input NE3, the control unit S then generates a measured value GW in step S103. In a next transmission step S104, which corresponds to the transmission step S7 from FIG. 3a, the data message of the second type DN2 is then sent to the network unit NI, and this data message of the second type DN2 has the measured gas value GW.

This process according to FIG. 7b may be advantageous when, for example, a transmission of the measured gas value GW via the wireless interface DGV of the gas-measuring device GV in FIG. 1b to the data interface D2 of the checking unit K in FIG. 1a is not possible, but the gas-measuring device GV in FIG. 1b has, for example, a display unit, so that the user can then input the measured value, which can be read there, into the checking unit.

Provisions may preferably be made for the checking unit or the control unit thereof to be configured to bring about a so-called pairing with a gas-measuring device in the sense of a logical data transmission coupling. Such a pairing is known, for example, as a Bluetooth Pairing. It is consequently guaranteed hereby based on a logical data transmission coupling that the checking unit or the control unit thereof is not connected to any random gas-measuring device for the data transmission and for the transmission of measured gas values, but a certain gas-measuring device was selected for this due to this logical data transmission coupling ("pairing") being brought about.

Figure 8A:
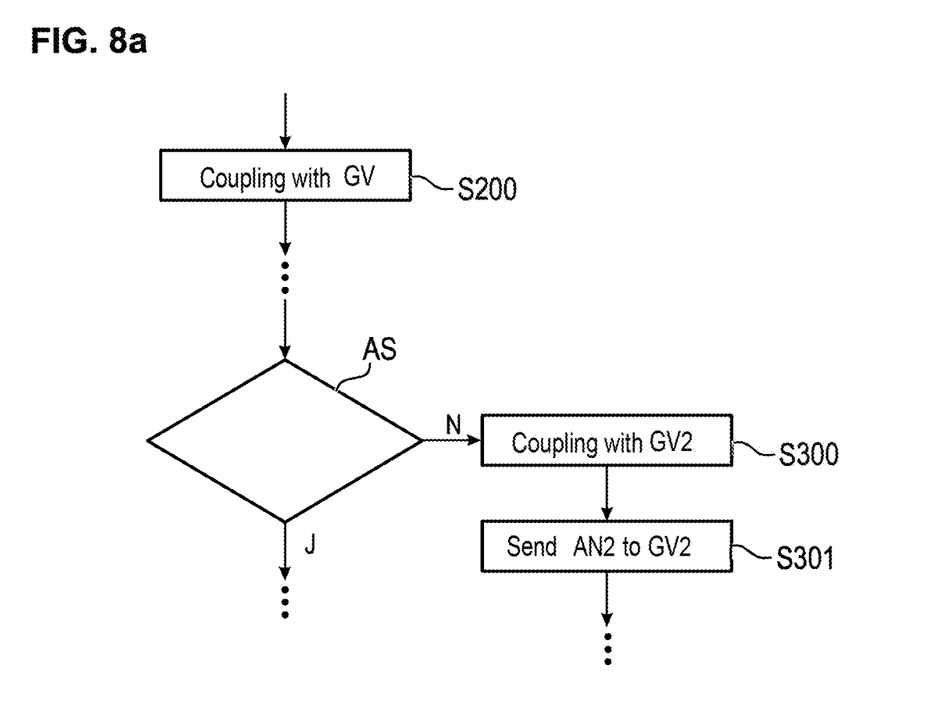
FIG. 8*a* is a view showing preferred process steps for a logical data transmission coupling of the checking unit with a gas-measuring device.

According to FIG. 8a, provisions may consequently be made in a step S200 for the control unit S to carry out a data exchange via the second data interface D2 with the gas-measuring device GV, which data exchange leads to a logical data transmission coupling being brought about between the checking unit K or the control unit S and the gas-measuring device GV.

If the derivation step AS from FIG. 2a or else AS1, AS2 from FIGS. 2b, 2c is then carried out later, it may happen that it is determined that no gas sensor type corresponding to the predefined type of gaseous substance is present in the gas-measuring device. It may become necessary now for the control unit or the checking unit to bring about a new or additional logical data transmission coupling with an additional or other gas-measuring device.

Therefore, provisions are then made for the control unit to carry out a data exchange in a step S300 for bringing about a further logical data transmission coupling between the checking unit or the control unit and the additional measuring device.

If this coupling has then been established, the further process step S301 will follow. The process step S301 corresponds essentially to the process step S5 from FIG. 3, in which the process described there is then continued by sending the third request message AN3.

Figure 8B:
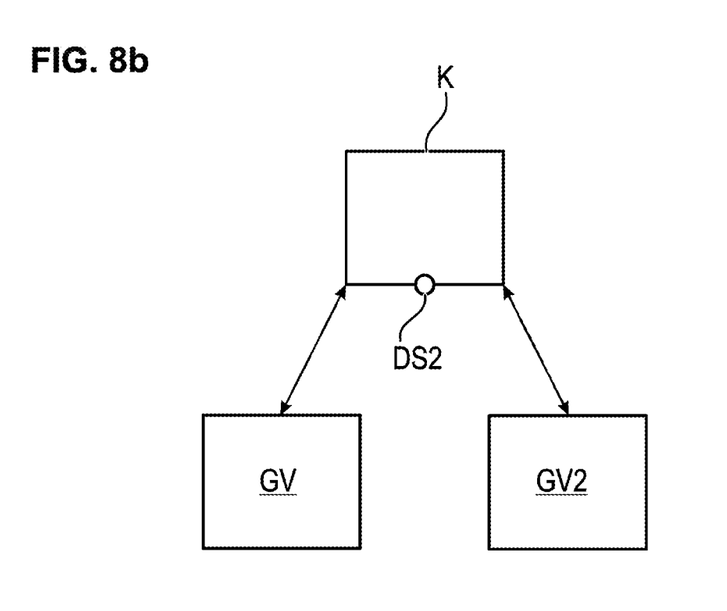
FIG. 8*b* is a schematic view of the checking unit according to the present invention together with a plurality of gas-measuring devices.

Consequently, the control unit S is configured now to derive via the two data interfaces whether a gas sensor type, which corresponds to the predefined type of gaseous substance, is present in the additional gas-measuring device, with which it is now coupled. The checking unit K with the two gas-measuring devices GV and GV2, which are mentioned as examples, is shown in FIG. 8b.

Even though some aspects were described in connection with a process or with a device, it is obvious that these aspects also represent a description of the corresponding device and of the corresponding process, so that a block or a component of a device can also be defined as a corresponding process step or as a feature of a process step and vice versa. Analogously hereto, aspects that were described in connection with a process step or as a process step also represent a description of a corresponding block or detail or feature of a corresponding device.

Depending on certain implementation requirements. exemplary embodiments of the present invention, especially the control unit, may be implemented in hardware or in software. The implementation may be carried out with the use of a digital storage medium, for example, a floppy disk, a DVD, a Blu-Ray disc, a CD, a ROM, a PROM, an EPROM, an EEPROM or a FLASH memory, a hard drive or another magnetic or optical memory, on which electronically readable control signals are stored, which can or do interact with a programmable hardware component such that the respective process is carried out.

A programmable hardware component may be formed by a processor, a computer processor (CPU=Central Processing Unit), a graphics processor (GPU=Graphics Processing Unit), a computer, a computer system, an application-specific integrated circuit (ASIC=Application-Specific Integrated Circuit), an integrated circuit (IC=Integrated Circuit), a system on chip (SOC=System on Chip), a programmable logic element or a field-programmable gate array with a microprocessor (FPGA=Field Programmable Gate Array).

The digital storage medium may therefore be machine- or computer-readable. Some exemplary embodiments consequently comprise a data storage medium, which has electronically readable control signals, which are capable of interacting with a programmable computer system or with a programmable hardware component such that one of the processes being described here is carried out. An exemplary embodiment is thus a data storage medium (or a digital storage medium or a computer-readable medium), on which the program for carrying out one of the processes being described here is recorded.

Exemplary embodiments of the present invention may generally be implemented as a program, firmware, computer program or computer program product with a program code or as data, wherein the program code or the data acts or act such as to carry out a process if the program is running on a processor or on a programmable hardware component. The program code or the data may also be stored, for example, on a machine-readable medium or data storage medium. The program code or the data may be present, among other things, as source code, machine code or byte code as well as another intermediate code.

Another exemplary embodiment is, furthermore, a data stream, a signal sequence or a sequence of signals, which data stream or sequence of signals represents one of the processes described here. The data stream, the signal sequence or the sequence of signals may be configured, for example, such as to be transferred via a data communication connection, for example, over the Internet or another network. Exemplary embodiments are consequently also signal sequences representing data, which signal sequences are suitable for transmission via a network or a data communication connection, wherein the data represent the program.

A program according to an exemplary embodiment may implement one of the processes during its execution, for example, by said program reading memory locations or writing one datum or a plurality of data into these memory locations, as a result of which switching operations or other operations are elicited in transistor structures, in amplifier structures or in other electrical, optical, magnetic components or in components operating according to another principle of function. Data, values, sensor values or other pieces of information can be correspondingly detected, determined or measured by a program by reading a memory location. By reading one or more memory locations, a program can therefore detect, determine or measure variables, values, measured variables and other pieces of information as well as bring about, trigger or carry out an action as well as actuate other devices, machines and components by writing into one or more memory locations.

The above-described exemplary embodiments represent only an illustration of the principles of the present invention. It is obvious that modifications and variations of the devices and details described here will be clear to other persons skilled in the art. It is therefore intended that the present invention shall be limited only by the scope of protection of the following patent claims and not by the specific details, which were presented here on the basis of the description and the explanation of the exemplary embodiments.

While specific embodiments of the invention have been shown and described in detail to illustrate the application of the principles of the invention, it will be understood that the invention may be embodied otherwise without departing from such principles.

The invention claimed is:

1. A checking unit for checking a gas-measuring device, the checking unit comprising:
   a first data interface;
   a second data interface; and
   a control unit configured:
      to receive a first request message, which indicates a request for providing at least one measured gas value of a predefined type of gaseous substance from a network unit via the first data interface;
      to transmit a second request message, which has a request for sending information related to a potential presence of at least one gas sensor type of the gas-measuring device to the gas-measuring device via the second data interface;
      to receive a reply message, which has the information related to the potential presence of the at least one gas sensor type, from the gas-measuring device via the second data interface;
      to derive from the information of the reply message whether a gas sensor type that corresponds to the predefined type of gaseous substance is present in the gas-measuring device; and,
      in a case of a derivation result of gas sensor type presence, to send a third request message to the gas-measuring device, which indicates a request to transmit the at least one measured gas value of the predefined type of gaseous substance to the control unit and to provide the at least one measured gas value to the network unit upon receipt of the at least one measured gas value.

2. The checking unit in accordance with claim 1, wherein the second request message has a request to send configuration information, which indicates gas sensor types that are indeed present in the gas-measuring device,
   the reply message has the configuration information, and
   the control unit derives from the type of gaseous substance and from the configuration information whether a gas sensor type corresponding to the type of gaseous substance is present in the gas-measuring device.

3. The checking unit in accordance with claim 2, further comprising a user interface, wherein the control unit is further configured to determine the measured gas value of the predefined type of gaseous substance on the basis of a user input into the user interface and to transmit it to the network unit by means of a data message of a second type in case a gas sensor type corresponding to the predefined type of gaseous substance is not present in the gas-measuring device.

4. The checking unit in accordance with claim 1, wherein
   the second request message has information that indicates the predefined type of gaseous substance or a gas sensor type corresponding to the predefined type of gaseous substance,
   the reply message has information, which indicates whether a gas sensor type corresponding to the predefined type of gaseous substance is present in the gas-measuring device, and
   the control unit derives from the information of the reply message whether a gas sensor type that corresponds to the predefined type of gaseous substance is present in the gas-measuring device.

5. The checking unit in accordance with claim 4, further comprising a user interface, wherein the control unit is further configured to determine the measured gas value of the predefined type of gaseous substance on the basis of a user input into the user interface and to transmit it to the network unit by means of a data message of a second type in case a gas sensor type corresponding to the predefined type of gaseous substance is not present in the gas-measuring device.

6. The checking unit in accordance with claim 1, wherein the control unit is configured
   to send the third request message via the second data interface to the gas-measuring device,
   to receive via the second data interface the at least one data message of a first type, which indicates the at least one measured gas value of the predefined type of gaseous substance, and
   to send a data message of the second type, which indicates the at least one measured gas value of the predefined type of gaseous substance to the network unit via the first data interface upon receipt of the at least one data message in case a gas sensor type that corresponds to the predefined type of gaseous substance is present in the gas-measuring device.

7. The checking unit in accordance with claim 6, wherein the third request message further indicates a request to detect the at least one measured gas value of the predefined type of gaseous substance by means of the gas-measuring device.

8. The checking unit in accordance with claim 6, further comprising a user interface and wherein the control unit is further configured to transmit the data message of the second type via the first data interface to the network unit as a function of an input of a user in the user interface.

9. The checking unit in accordance with claim 8, further comprising an optical display unit, wherein the control unit is further configured
   to receive via the second data interface a plurality of data messages of the first type, which indicate a plurality of measured gas values,
   to select from the plurality of measured gas values a current measured gas value as well as at least one additional measured gas value and to output the selected measured gas values by means of the optical display unit to the user, and
   to select one of the outputted measured gas values as a function of a user input of the user into the user interface and to transmit the at least one measured gas value of the predefined type of gaseous substance to the network unit by means of the data interface of the second type.

10. The checking unit in accordance with claim 8, wherein the control unit is further configured
    to generate a measured value data set on the basis of the at least one measured gas value,
    to receive a predefined value data set, to generate a digital signature of the at least one measured value data set on the basis of the predefined value data set and of the at least one measured value data set, and to transmit the at least one measured gas value of the predefined type of gaseous substance in the form of the measured value data set and of the digital signature to the network unit by means of the data interface of the second type.

11. The checking unit in accordance with claim 6, wherein the control unit is further configured to transmit to the network unit via the second data interface an information message, which indicates that the at least one measured gas value of the predefined type of gaseous substance cannot be provided in case a gas sensor type corresponding to the predefined type of gaseous substance is not present in the gas-measuring device.

12. The checking unit in accordance with claim 1, wherein the control unit is further configured to carry out a data exchange with the gas-measuring device via the second data interface to bring about a data transmission coupling between the checking unit and the gas-measuring device, and to carry out a data exchange with an additional gas-measuring device via the second data interface to bring about another data transmission coupling between the checking unit and the additional gas-measuring device in case no gas sensor type corresponding to the predefined type of gaseous substance is present in the gas-measuring device, and to derive by means of a data exchange with the additional gas-measuring device via the second data interface whether a gas sensor type that corresponds to the predefined type of gaseous substance is present in the additional gas-measuring device, to send the third request message to the additional gas-measuring device and to provide this at least one measured gas value for the network unit upon receipt of the at least one measured gas value of the predefined type of gaseous substance in the case of a positive derivation result.

13. A process for checking a gas-measuring device, the process comprising the steps of:

receiving a first request message from a network unit via a first data interface, wherein the first request message indicates a request for detecting at least one measured gas value of a predefined type of gaseous substance;

transmitting a second request message to the gas-measuring device via a second data interface, wherein the second request message has a request for sending information related to a potential presence of at least one gas sensor type of the gas-measuring device, receiving a reply message from the gas-measuring device via the second data interface, wherein the reply message has the information related to the potential presence of the gas sensor type, deriving, on the basis of the information of the reply message whether a gas sensor type that corresponds to the predefined type of gaseous substance is present in the gas-measuring device, sending, in case of a positive derivation result, a third request message to the gas-measuring device, which indicates a request for transmitting the at least one measured gas value of the predefined type of gaseous substance to the checking unit, and providing, upon receipt of the at least measured gas value, the at least one measured gas value to the network unit.

14. The process according to claim 13, further comprising providing a device with a computer, which is configured to carry out the process steps.

15. The process according to claim 13, further comprising a computer program with a program code for carrying out the process steps when the program code is executed on a computer, on a processor or on a programmable hardware component.

16. A checking unit for checking a gas-measuring device, the checking unit comprising:

a first data interface;

a second data interface; and a control unit configured:

to receive a first request message, which indicates a request for providing at least one measured gas value of a predefined type of gaseous substance from a network unit via the first data interface;

to transmit a second request message, which has a request for sending information related to a potential presence of at least one gas sensor type of the gas-measuring device directly to the gas-measuring device via the second data interface;

to receive a reply message, which has the information related to the potential presence of the at least one gas sensor type, directly from the gas-measuring device via the second data interface;

to determine from the information of the reply message whether a gas sensor type that corresponds to the predefined type of gaseous substance is present in the gas-measuring device; and, in a case of a determination of the gas sensor type corresponding to the predefined type of gaseous substance being present in the gas-measuring device, to send a third request message directly to the gas-measuring device, which indicates a request to transmit the at least one measured gas value of the predefined type of gaseous substance to the control unit and to provide the at least one measured gas value to the network unit upon receipt of the at least one measured gas value.

17. The checking unit in accordance with claim 16, wherein:

the second request message has a request to send configuration information, which indicates gas sensor types that are present in the gas-measuring device;

the reply message has the configuration information; and the control unit derives from the type of gaseous substance and from the configuration information whether a gas sensor type corresponding to the type of gaseous substance is present in the gas-measuring device.

18. The checking unit in accordance with claim 16, wherein:

the second request message has information that indicates the predefined type of gaseous substance or a gas sensor type corresponding to the predefined type of gaseous substance, the reply message has information, which indicates whether a gas sensor type corresponding to the predefined type of gaseous substance is present in the gas-measuring device, and the control unit derives from the information of the reply message whether a gas sensor type that corresponds to the predefined type of gaseous substance is present in the gas-measuring device.

19. The checking unit in accordance with claim 16, wherein the control unit is configured:

to send the third request message via the second data interface to the gas-measuring device;

to receive via the second data interface the at least one data message of a first type, which indicates the at least one measured gas value of the predefined type of gaseous substance; and to send a data message of the second type, which indicates the at least one measured gas value of the predefined type of gaseous substance to the network unit via the first data interface upon receipt of the at least one data message in case a gas sensor type that corresponds to the predefined type of gaseous substance is present in the gas-measuring device.

20. The checking unit in accordance with claim 19, wherein the third request message further indicates a request to detect the at least one measured gas value of the predefined type of gaseous substance by means of the gas-measuring device.

* * * * *